(12) United States Patent
Tu

(10) Patent No.: US 6,764,454 B2
(45) Date of Patent: Jul. 20, 2004

(54) FITNESS STICK WITH MOXIBUSTION AND PATTING BAT

(76) Inventor: Chin-Sheng Tu, 2/F, No. 79, Ji-Lin Rd., Taipei (TW)

( * ) Notice: Subject to any disclaimer, the term of this patent is extended or adjusted under 35 U.S.C. 154(b) by 177 days.

(21) Appl. No.: 10/207,599

(22) Filed: Jul. 27, 2002

(65) Prior Publication Data

US 2004/0019305 A1 Jan. 29, 2004

(51) Int. Cl.⁷ .............................. A61H 23/06; A61H 7/00
(52) U.S. Cl. ....................... 601/15; 601/107; 601/120; 601/121; 601/135; 606/27
(58) Field of Search ........................... 601/15, 17, 107, 601/109, 118, 119, 120, 121, 122, 124, 127, 129, 130, 132, 134, 135; 482/44–46, 79, 109; 604/24, 291; 606/27; 607/96

(56) References Cited

U.S. PATENT DOCUMENTS

| | | | |
|---|---|---|---|
| 1,817,823 A | * | 8/1931 | Ito .............................. 604/24 |
| 4,671,788 A | * | 6/1987 | Wu ............................. 604/24 |
| 4,731,050 A | * | 3/1988 | Harada et al. ................ 604/24 |
| 6,461,377 B1 | * | 10/2002 | An ............................. 601/15 |
| 2004/0024336 A1 | * | 2/2004 | Lin ............................ 601/107 |

FOREIGN PATENT DOCUMENTS

| | | | | |
|---|---|---|---|---|
| JP | 405329190 A | * | 12/1993 | .......... A61H/39/06 |
| JP | 02003260110 A | * | 9/2003 | .......... A61H/39/06 |

* cited by examiner

Primary Examiner—Danton D. DeMille
Assistant Examiner—Quang D. Thanh
(74) Attorney, Agent, or Firm—Pro-Techtor International Services

(57) ABSTRACT

The present invention is related to a fitness stick and particularly to a fitness stick with a sheath and a moxibustion instrument, comprising a flapping bat, a sheath and a moxibustion instrument, having many protuberances on the surface of sheath for massaging, the moxibustion instrument is assembled inside the handle of the flapping bat with a separable spring coil and could be separated from the stick for isolated use with both functions of moxibustion and massage.

11 Claims, 23 Drawing Sheets

FITNESS STICK WITH MOXIBUSTION AND PATTING BAT

BACKGROUND OF THE INVENTION

The conventional flapping bat is unable to perform the function of moxibustion of massaging. The flapping of commercial available flapping bats, made from bundles of bamboo stick, on human skin may lead to fracture and piercing. Such bamboo-made flapping bat could only flap the surface of human body to stimulate the neurovascular system in the superficial layer and therefore is only able to eliminate local hematoma but not able to stimulate the physique and muscle in the deeper layer. Thus, flapping by using such bamboo-made bat could not increase the tension and elasticity of muscles, tendons, and ligaments, and could not enhance the capability for contraction nor activities. Apart from being used for therapy, such bamboo-made flapping bat could not be utilized for fitness.

In view of above, the present invention offers a fitness stick and particularly to a fitness stick with a sheath and a moxibustion instrument, comprising a flapping bat, a sheath and a moxibustion instrument, having many protuberances on the surface of sheath for massaging, the moxibustion instrument is assembled inside the handle of the flapping bat with a separable spring coil and could be separated from the stick for isolated use with both functions of moxibustion and massage. While assembled inside the handle of flapping bat without being screwed with the handle, this moxibustion instrument is the spring device of this fitness stick. After the spring coil disassembly and being replaced to sheath of the fitness stick, the moxibustion instrument could also be used as the spring device to enable the functions of moxibustion and massage, in addition to flapping, of this fitness stick.

SUMMARY OF THE INVENTION

The principal object of this invention is to provide a fitness stick for flapping, moxibustion and massaging.

DESCRIPTION OF THE PREFERRED EMBODIMENTS

Figure 1:
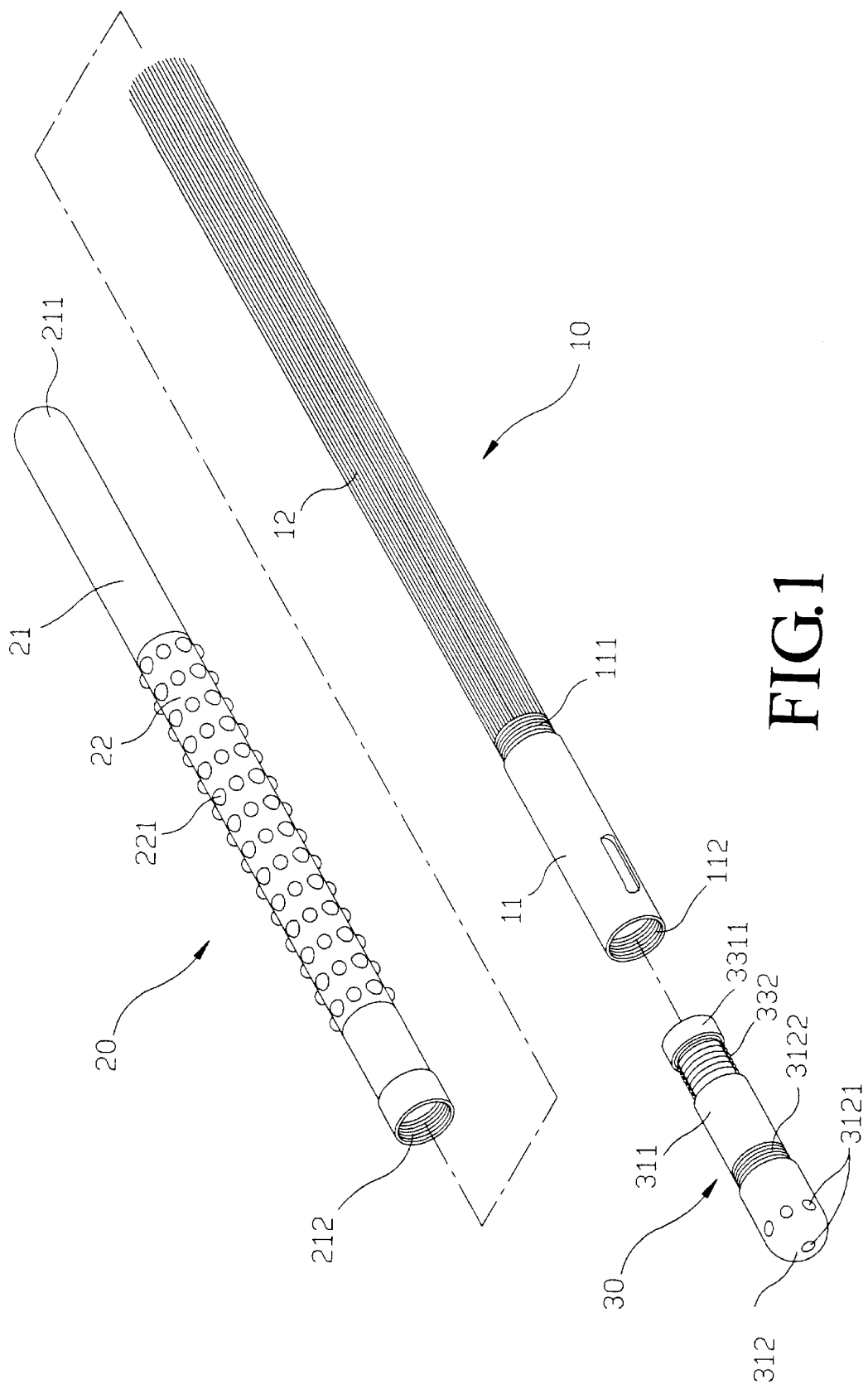
FIG. 1 is a breakdown view of a preferred embodiment of fitness stick according to the present invention.

Other objects and features of the present invention will become apparent from a consideration of the following description which proceeds with reference to the accompanying drawings wherein certain selected embodiments are chosen to illustrate the invention.

As shown in FIGS. 1 to 4, a fitness stick 1 comprising a flapping bat 10, a sheath 20 and a moxibustion instrument 30, wherein the flapping bat 10 primarily consists of a handle 11 and a bundle of iron strip 12. The external edge of front end of handle 11 is provided with a thread of screw 111, and the back end of handle 11 is provided with a screw hole 112. The bundle of iron strip 12 consists of a plurality of stainless steel with a same diameter and length and ligated to the interior side of front end of handle 11.

Figure 2:
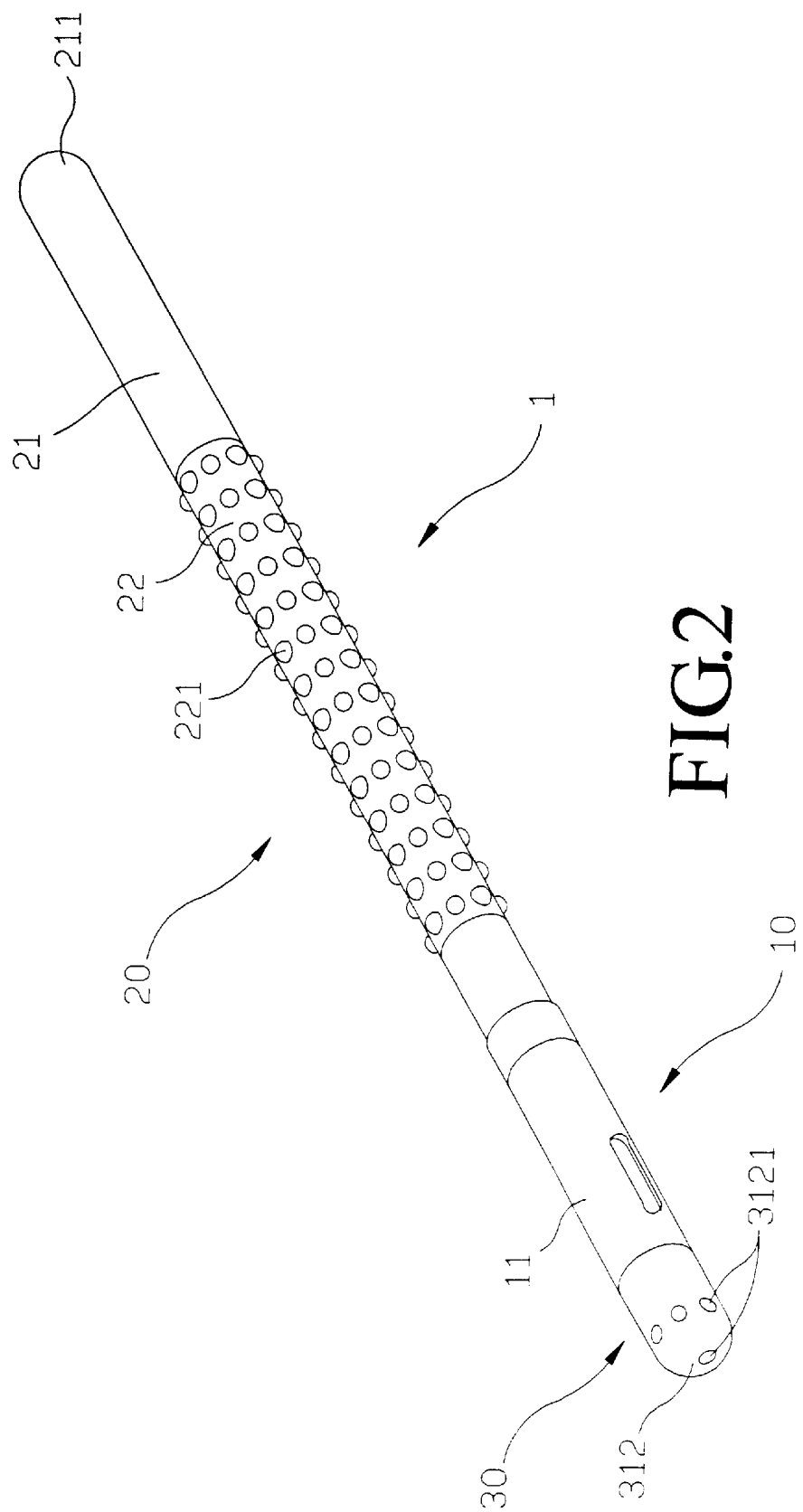
FIG. 2 is a perspective view of a preferred embodiment of fitness stick according to the present invention.
Figure 3:
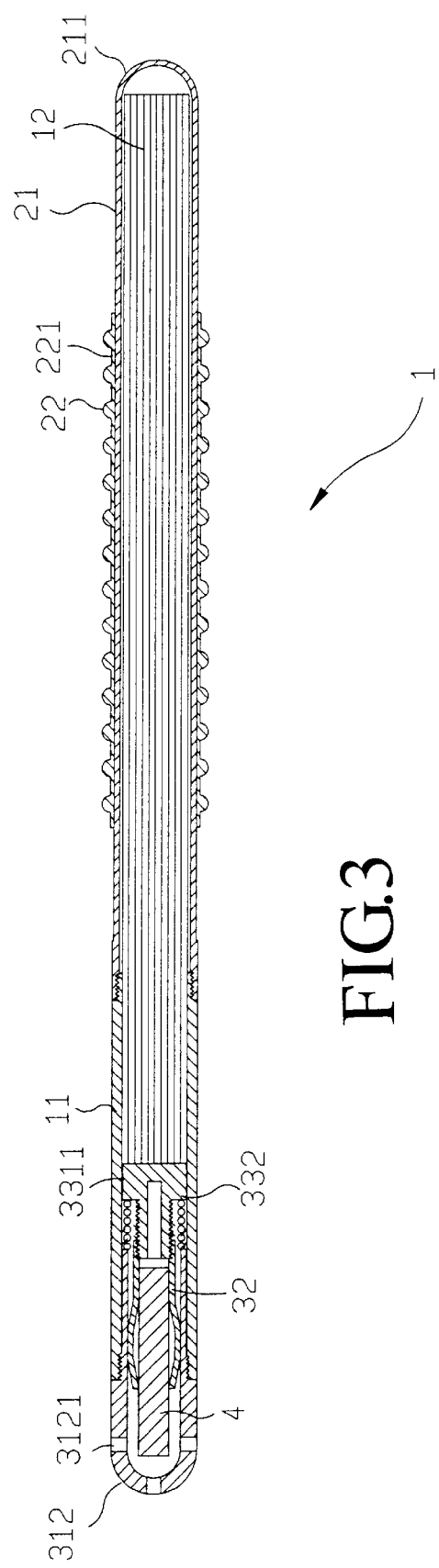
FIG. 3 is a cross section view of the embodiment of FIG. 2.
Figure 4:
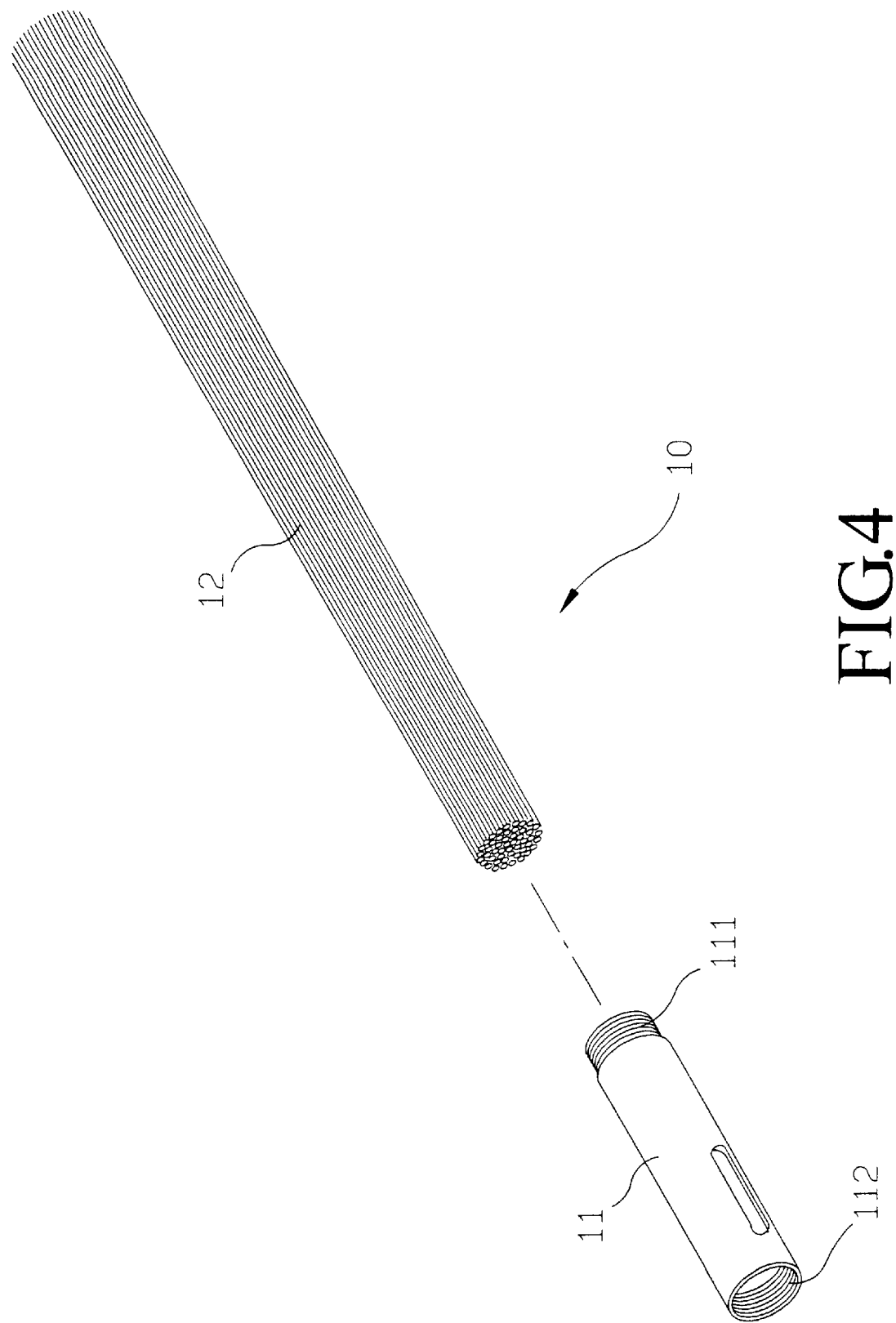
FIG. 4 is a breakdown view of the flapping bat of fitness stick of the embodiment of the present invention.
Figure 5:
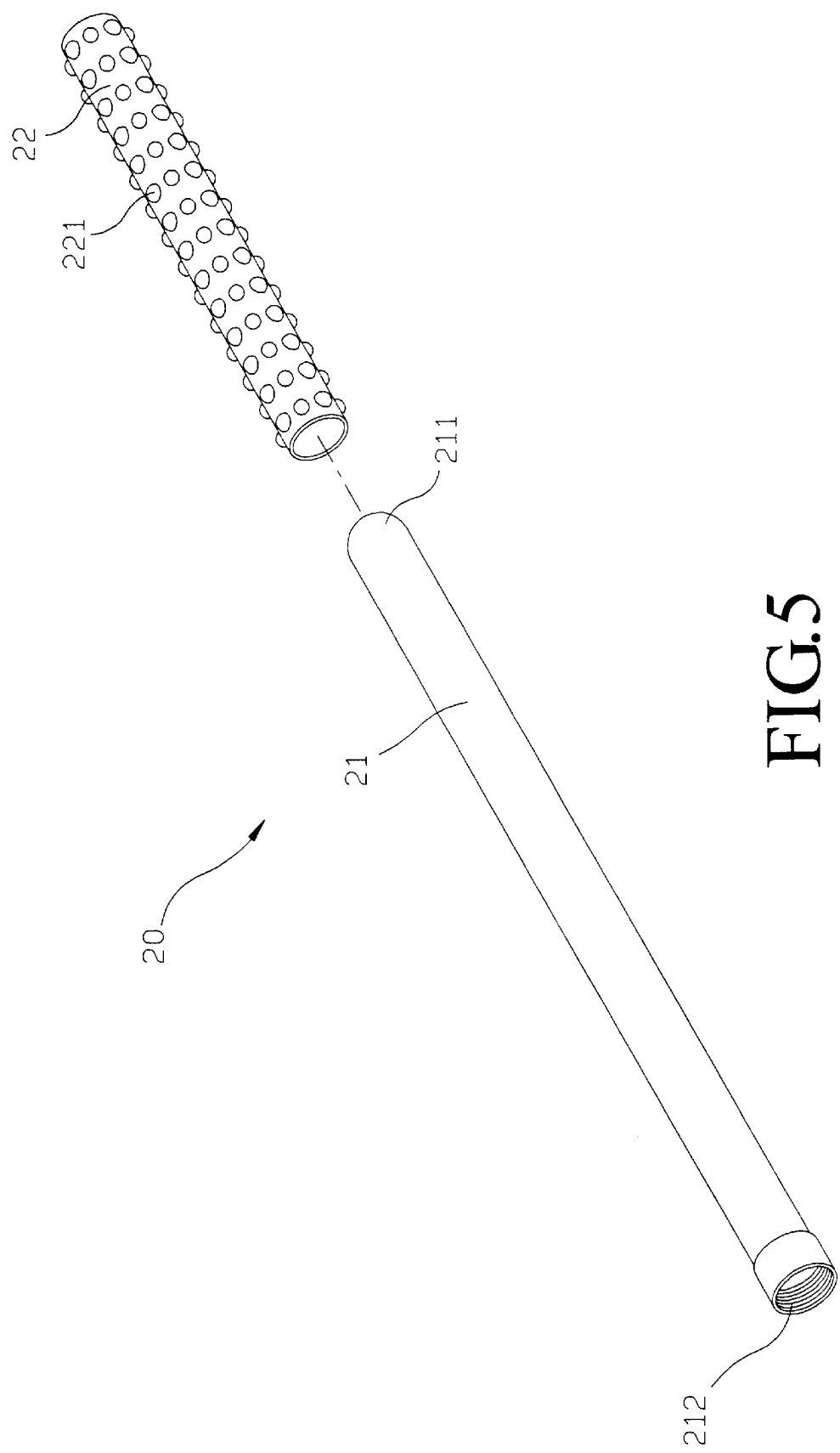
FIG. 5 is a breakdown view of the sheath of fitness stick of the embodiment of the present invention.

As shown in FIGS. 1 and 5, the sheath 20 consists of a covering shaft 21 and a massaging sleeve 22, the front end of covering shaft 21 is provided with a semicircle arc cap 211, and the back end of covering shaft 21 is provided with a screw hole 212, and the diameter of the covering shaft 21 is the same as that of handle 11 of the flapping bat 10, and the length of the covering shaft 21 is slightly longer than or the same as that of the bundle of iron strip 12 located at the outside the handle 11 of flapping bat 10. This bundle of iron strip 12 outside the handle 11 of flapping bat 10 is just able to slide into the covering shaft 21 via the screw hole 212 at the back end of covering shaft 21. The surface of massaging sleeve 22 of sheath 20 is provided with many protuberances 221. The massaging sleeve 22 is just able to cover the covering shaft 21 to form a sheath 20 with many surface protuberances 221 and massaging function. As shown in FIGS. 2 and 3, while the bundle of iron strip 12, which is located at outside of handle 11 of flapping bat 10, is completely placed into the covering shaft 21 via the screw hole 212 at the back end of covering shaft 21, the thread of screw 111 at the external edge of the front end of handle 11 is just able to enter the screw hole 212 at the back end of covering shaft 21 to integrate the covering shaft 21 and handle 11 by screwing.

Figure 6:
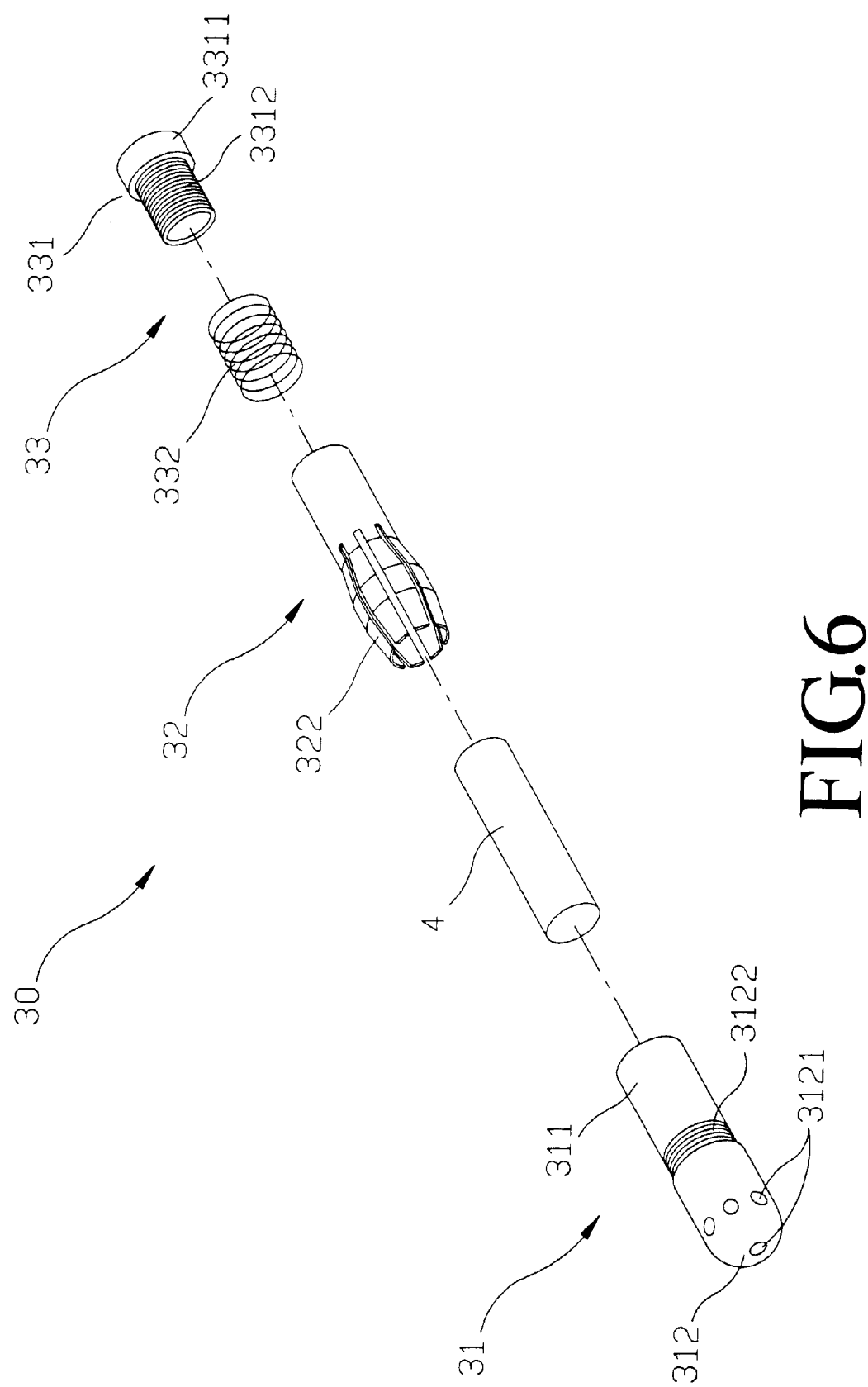
FIG. 6 is a breakdown view of the moxibustion instrument of fitness stick of the embodiment of the present invention.
Figure 7:
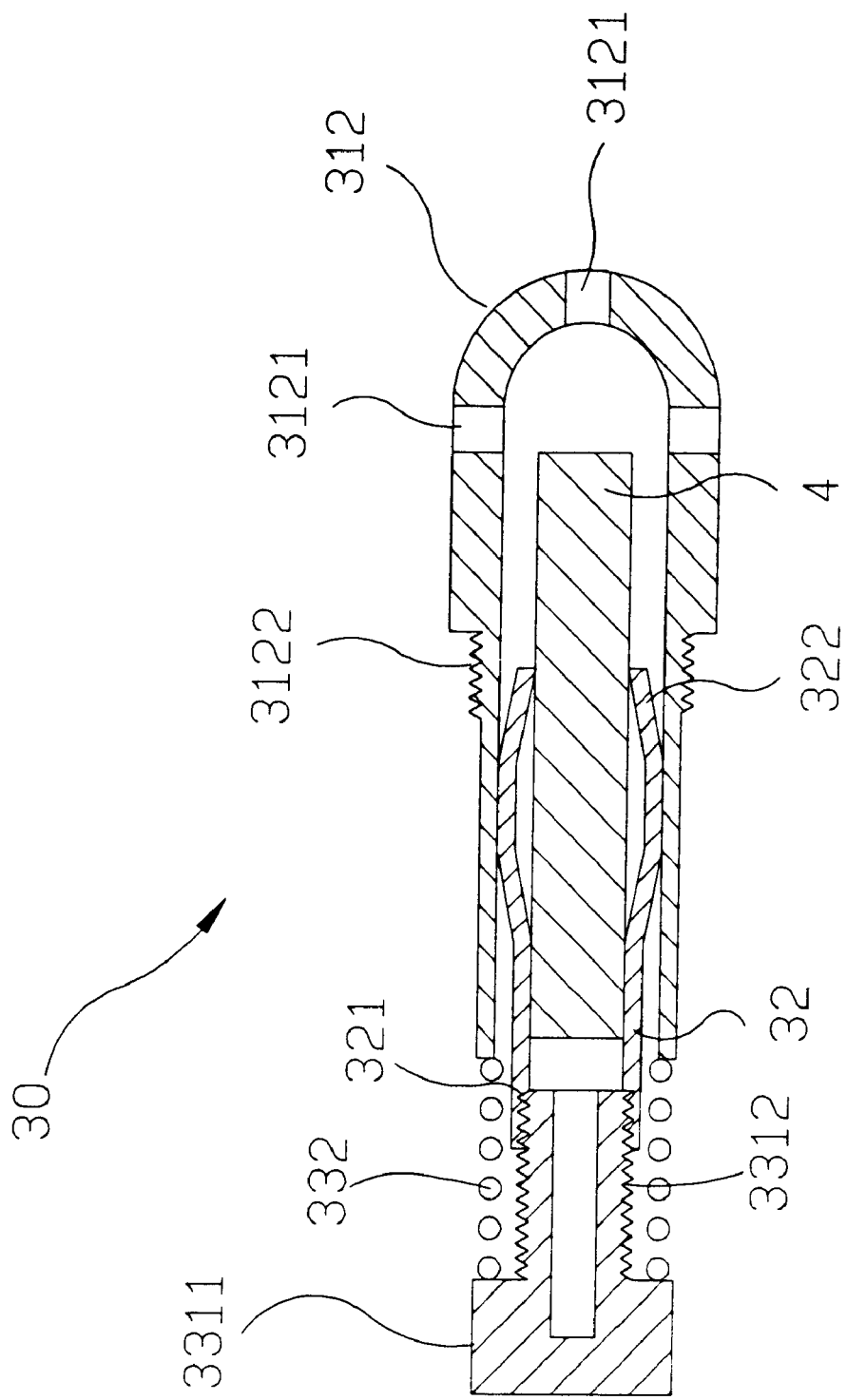
FIG. 7 is a cross section of the moxibustion instrument of fitness stick of the embodiment of the present invention.

As shown in FIGS. 1, 6 and 7, the moxibustion instrument 30 of fitness stick 1 comprising a metal moxibustion cover 31, a clipping shaft 32 and a spring coil 33, wherein the metal moxibustion cover 31 consists of a hollow sleeve 311 and a semicircle arc moxibustion caps 312. The back end and periphery of the semicircle arc moxibustion cap 312 is provided with a plurality of vent holes 3121, and the neck of semicircle arc moxibustion caps 312 and the external edge of back connection site of the hollow sleeve 311 is provided with a thread of screw 3122. The outer diameter of hollow sleeve 311 of metal moxibustion cover 31 is equal to or slightly smaller than the inner diameter of handle 11 of flapping bat 10. As showing in FIGS. 1 and 2, while the front end of hollow sleeve 311 of metal moxibustion cover 31 is inserted from the back end of handle 11 of flapping bat 10, the thread of screw 3122 at the external edge of connection sites between the neck of semicircle arc moxibustion cap 312 of metal moxibustion cover 31 and the back end of hollow sleeve 311 is just able to screw into the screw hole 112 at the back end of handle 11 of flapping bat 10 to integrate all together.

As shown in FIG. 7, the front end of the clipping shaft 32 of the moxibustion instrument 30 is provided with a screw hole 321, and the back end of clipping shaft 32 is provided with a spring clip 322. The spring clip 322 of clipping shaft 32 is suitable for clipping a moxa stick 4.

Figure 9:
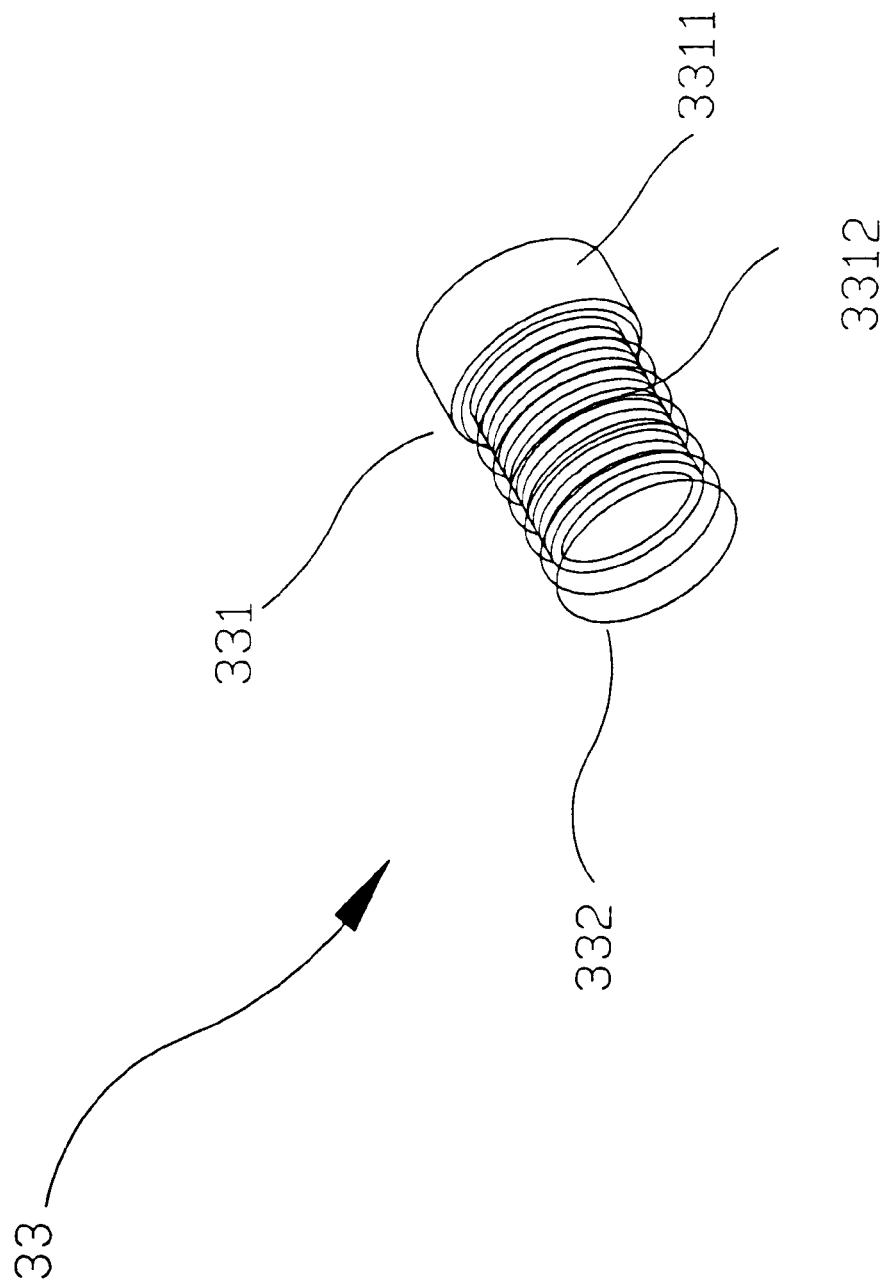
FIG. 9 is a perspective view of the spring coil of moxibustion instrument shown in FIGS. 6 and 7.
Figure 10:
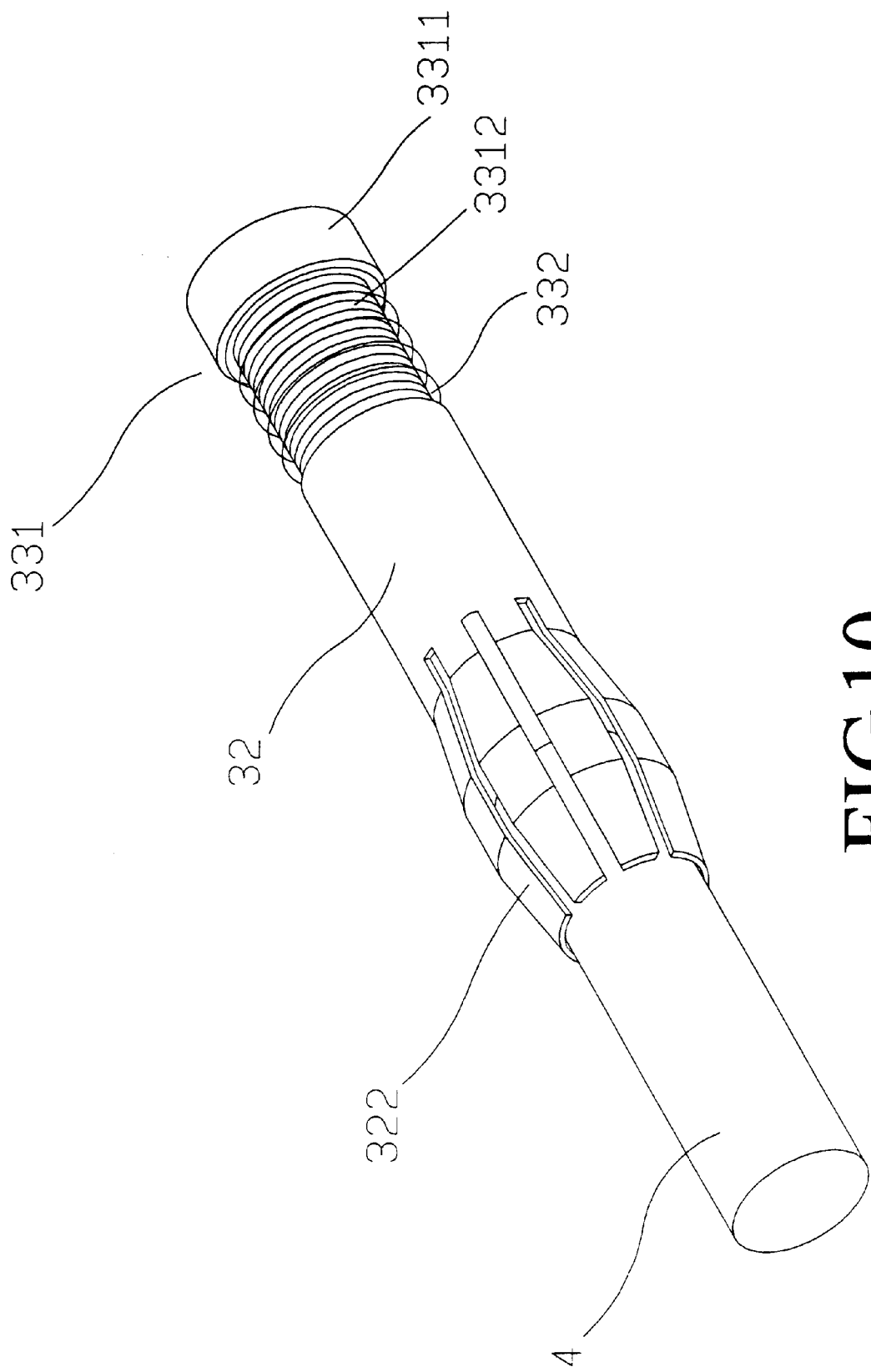
FIG. 10 is a perspective view of a clipping shaft and a spring coil of moxibustion instrument shown in FIGS. 6 and 8.

As shown in FIG. 9, the spring coil 33 of moxibustion 30 consists of a screw 331 and a spring 332, the spring 332 is connected to the external edge of screw shaft 3312 beneath the screw nut 3311 of screw 331. As shown in FIG. 10, the screw 331 of spring coil 33 is just right for screwing into the screw hole 321 located at the front end of clipping shaft 32 of moxibustion instrument 30 to integrate all together, the spring 322 of spring coil 33 is just suitable for slipping on the external edge of clipping shaft 32.

Figure 11:
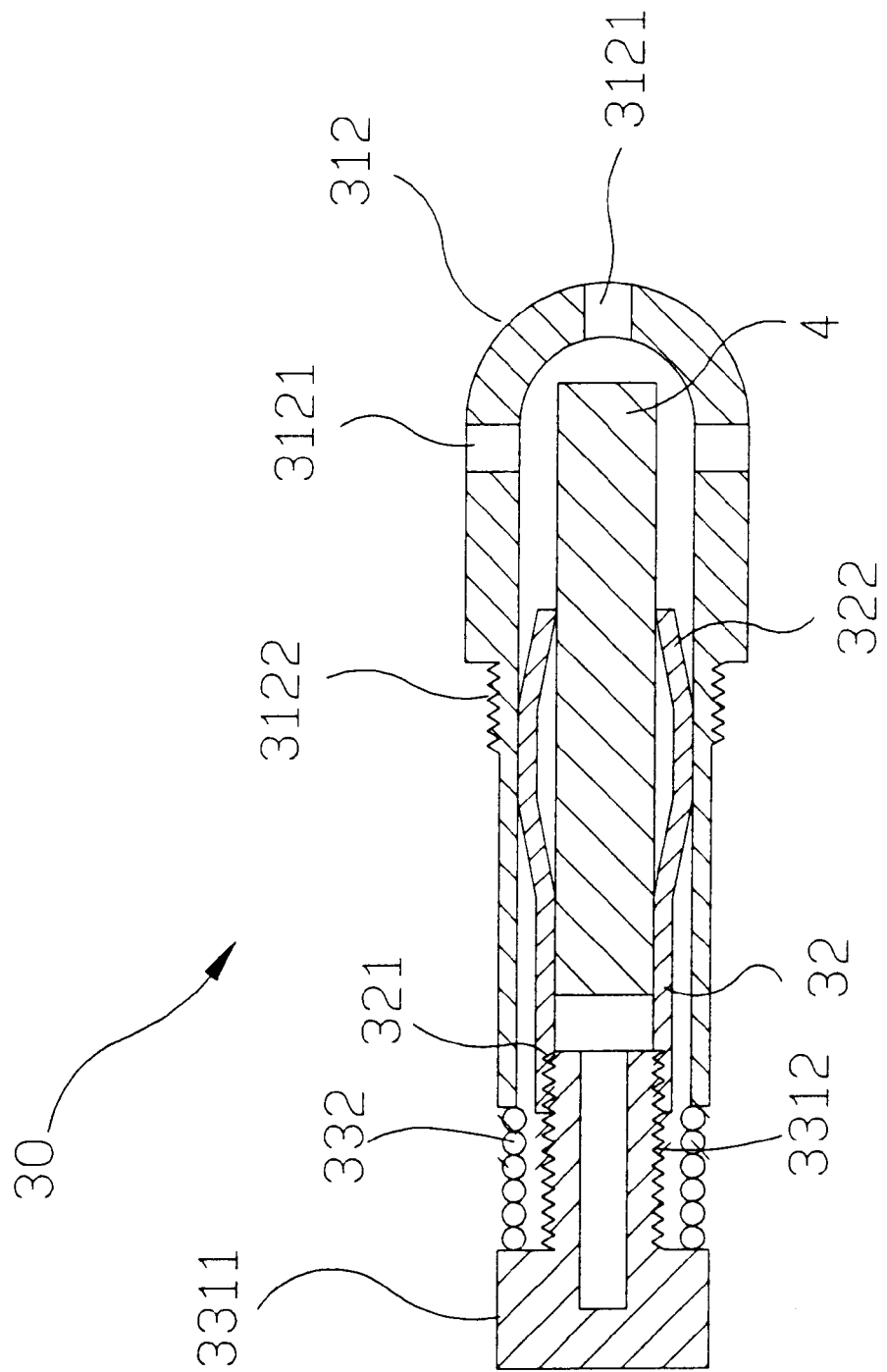
FIG. 11 is a cross section of compression of the moxibustion instrument on the spring coil induced by an external force shown in FIG. 7.

As shown in FIGS. 6 and 7, the spring clip 322 at the back end of clipping shaft 32 Is screwed with spring coil 33 to be a unity and just suitable for inserting into the hollow sleeve 311 of metal moxibustion cover 31 to form moxibustion instrument 30. For the time being, the tip of spring 322 of spring coil 33 which is slipped on the external edge of clipping shaft 32, is just against the front edge of hollow sleeve 311 of this metal moxibustion cover 31. As shown in FIGS. 7 and 11, the spring 332 of spring coil 33 slipped on the external edge of clipping shaft 32 can be compressed by pressurizing on the semicircle arc moxibustion cap 312 at the back end of hollow sleeve 311 of metal moxibustion cover 31. Furthermore, the spring 332 of spring coil 33 slipped on the external edge of clipping shaft 32 can be released by liberating the semicircle arc moxibustion cap 312 at the back end of hollow sleeve 311 of metal moxibustion cover 31.

As shown in FIGS. 12 to 15, by inserting the front end of spring coil 33 of moxibustion instrument 30 into the distal end of handle 11 of flapping bat 10 to slightly pressurize on the semicircle arc moxibustion cap 312 at the back end of hollow sleeve 311 of metal moxibustion cover 31, the spring 332 of spring coil 33 slipped on the external edge of clipping shaft 32 can be compressed. Then, the thread of screw 3122 at the external edge of connection sites between the neck of semicircle arc moxibustion cap 312 of metal moxibustion cover 31 and the back end of hollow sleeve 311 is just able to screw into the screw hole 112 at the back end of handle 11 of flapping bat 10 to Integrate as an unity. While compressing the spring 332 of spring coil 33 slipped on the external edge of clipping shaft 32 by pressurizing on the semicircle arc moxibustion cap 312 at the back end of hollow sleeve 311 of metal moxibustion cover 31, the thread of screw 3122 at the external edge of back connection sites between the neck of semicircle arc moxibustion cap 312 of metal moxibustion cover 31 and the back end of hollow sleeve 311 will contact with, but not screw into, the screw hole 112 at the back end of handle 11 of flapping bat 10. This moxibustion instrument 30, therefore, becomes the elastic device of fitness stick 1. Meanwhile, the spring 332 of spring coil 33 slipped on the external edge of clipping shaft 32 can be released by liberating the semicircle arc moxibustion cap 312 at the back end of hollow sleeve 311 of metal moxibustion cover 31.

Figure 16:
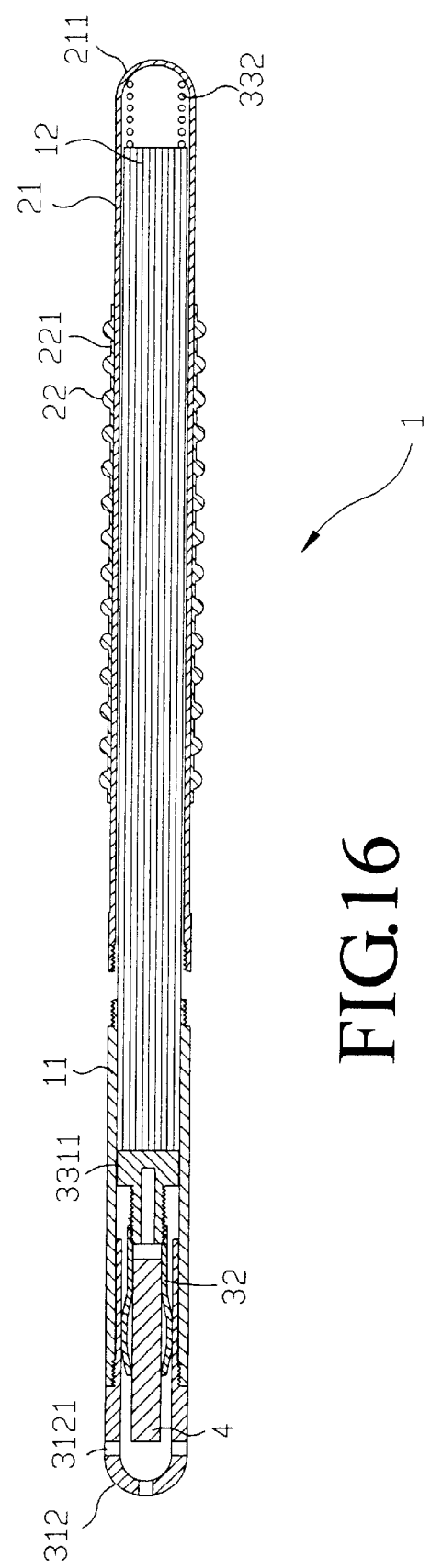
FIG. 16 is a cross section of the fitness stick shown in FIGS. 1 and 2, and disassembled spring coil of moxibustion instrument being replaced inside of sheath and contacting the proximal end of iron bundle of flapping bat.
Figure 17:
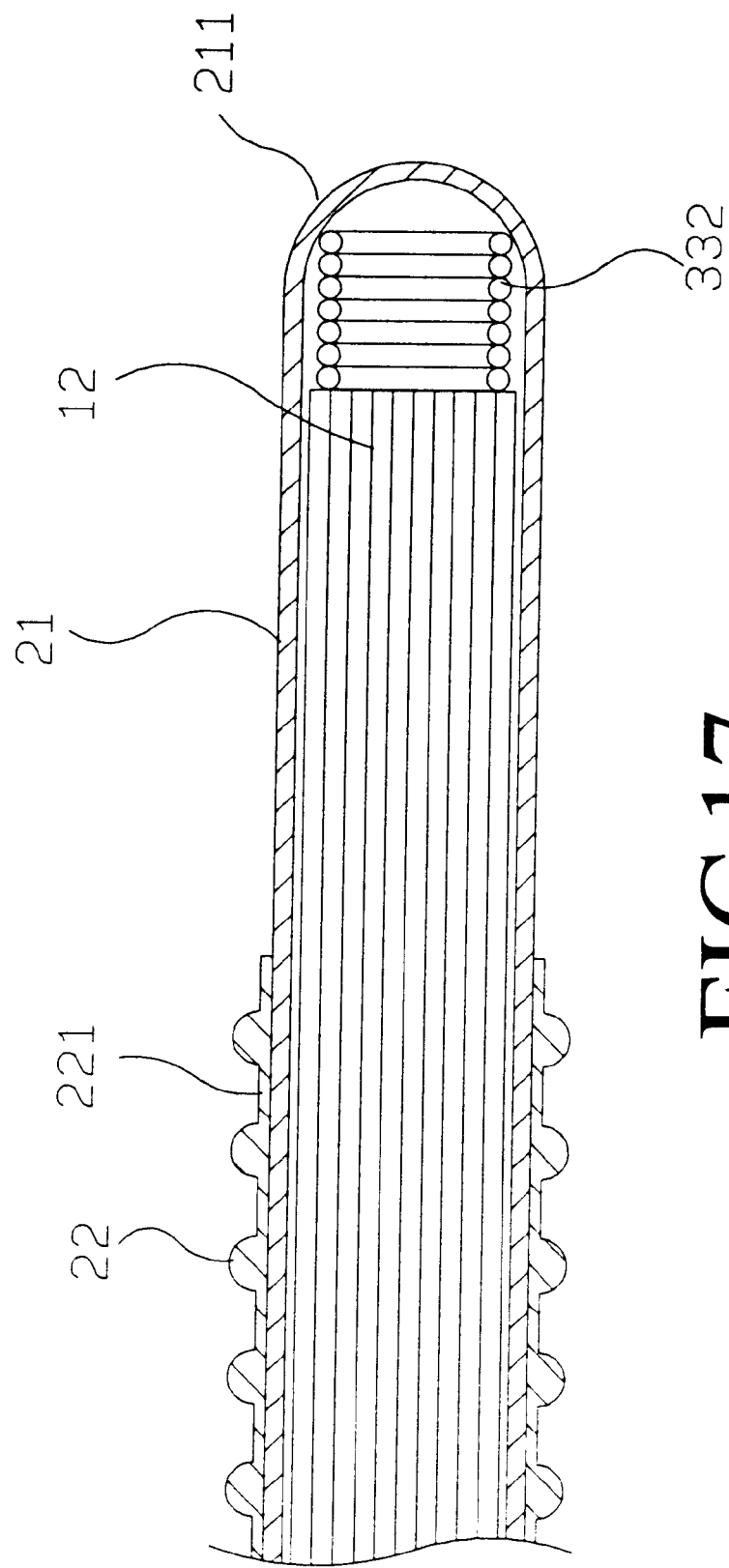
FIG. 17 is a cross section and in part cutaway view of compressed spring coil of iron bundle of flapping bat shown in FIG. 16.

As shown in FIG. 16, the moxibustion instrument 30 is removed from handle 11 of flapping bat 10 of fitness stick 1. Afterwards, spring coil 33 is disassembled from clipping shaft 32 of moxibustion instrument 30 and then replaced into the sheath 20 to use as elasticity device of fitness stick 1. While being restrained inside the sheath 20, the frond end of bundle of iron strip 12 of flapping bat 10 will collide with the screw nut 3311 of spring coil 33, which is replaced inside the sheath 20. As shown in FIG. 17, spring 322 of spring coil 33, which is replaced inside the sheath 20, can be compressed by pressurizing the back end of handle 11 of flapping bat 10 of fitness stick 1 or pressurizing the front end of sheath 20 of fitness stick 1 to make the flapping bat 10 and sheath 20 being compressed against each other.

The flapping of commercial available flapping bats, made from bundles of bamboo stick, on human skin may lead to fracture and piercing, such defects are absent in the flapping of fitness stick 1. In addition, flapping with fitness stick 1 can stimulate all sorts of neurovascular system in human body, as well as eliminate local hematoma, accelerate the blood circulation and ameliorate the nutrition status of all organs. Such flapping can stimulate the physique and muscle, increase the tension and elasticity of muscles, tendons, and ligaments, and enhance the capability for contraction and activities.

Figure 8:
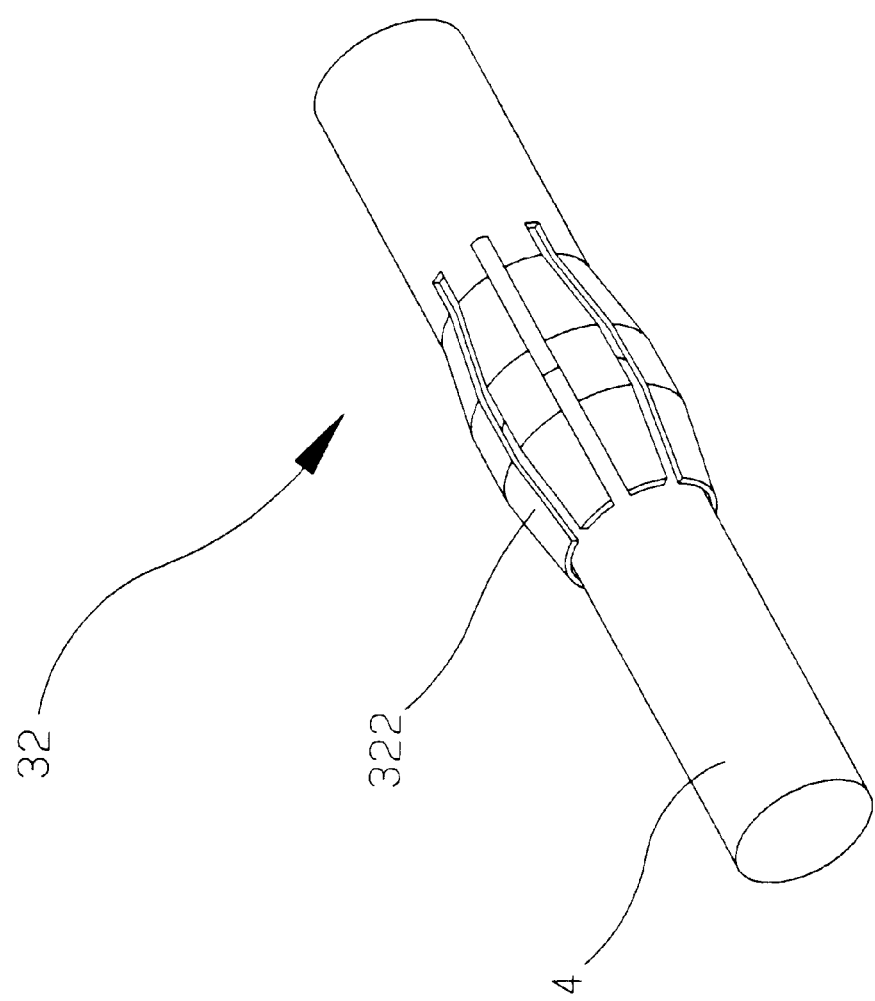
FIG. 8 is a perspective view of a moxa stick being holding by the spring clip, which is located at the distal end of clipping pen of the moxibustion instrument shown in FIGS. 6 and 7.
Figure 12:
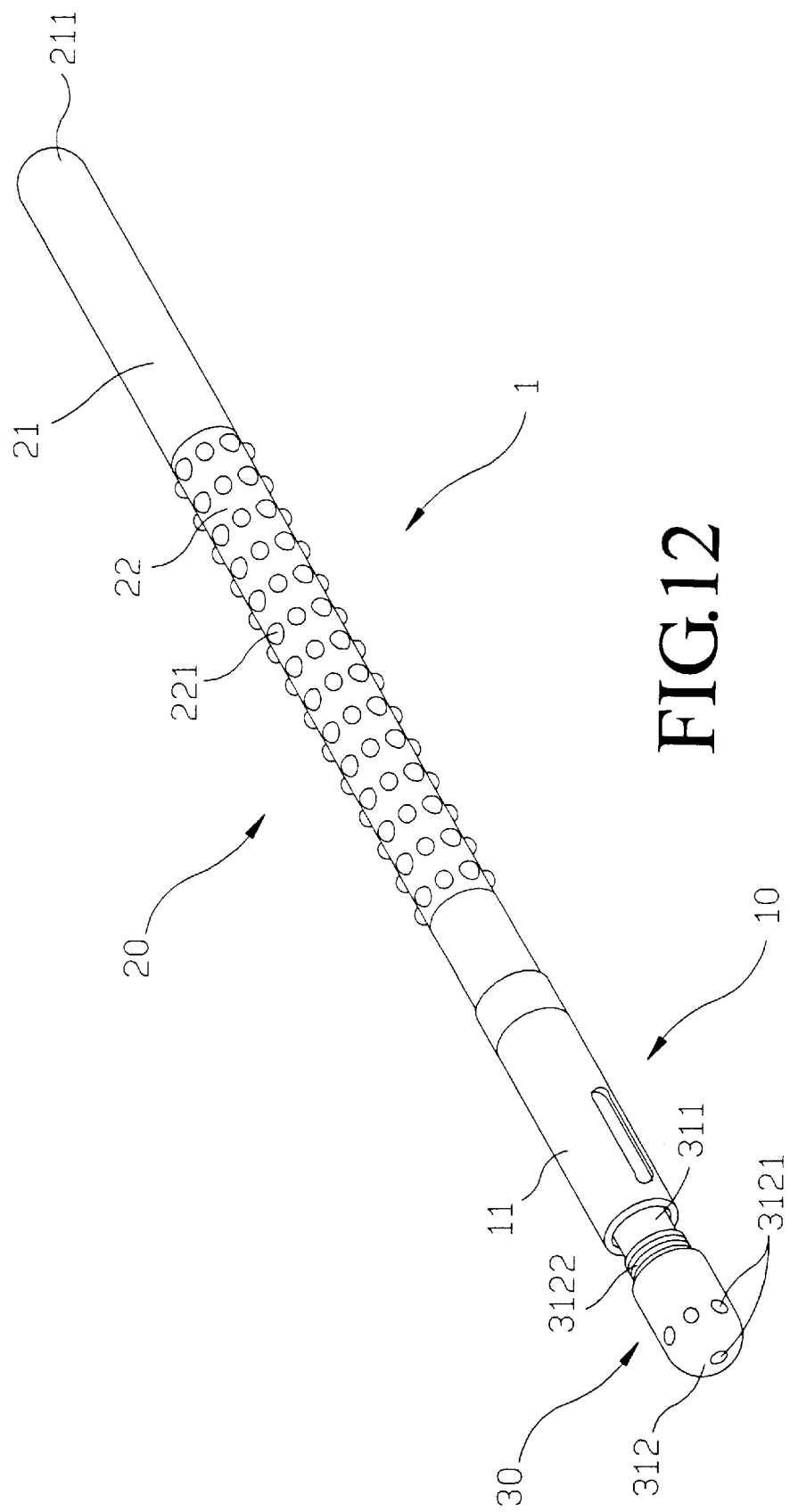
FIG. 12 is a perspective view of the moxibustion instrument not being screwed to handle of this fitness stick shown in FIGS. 2 and 7.
Figure 13:
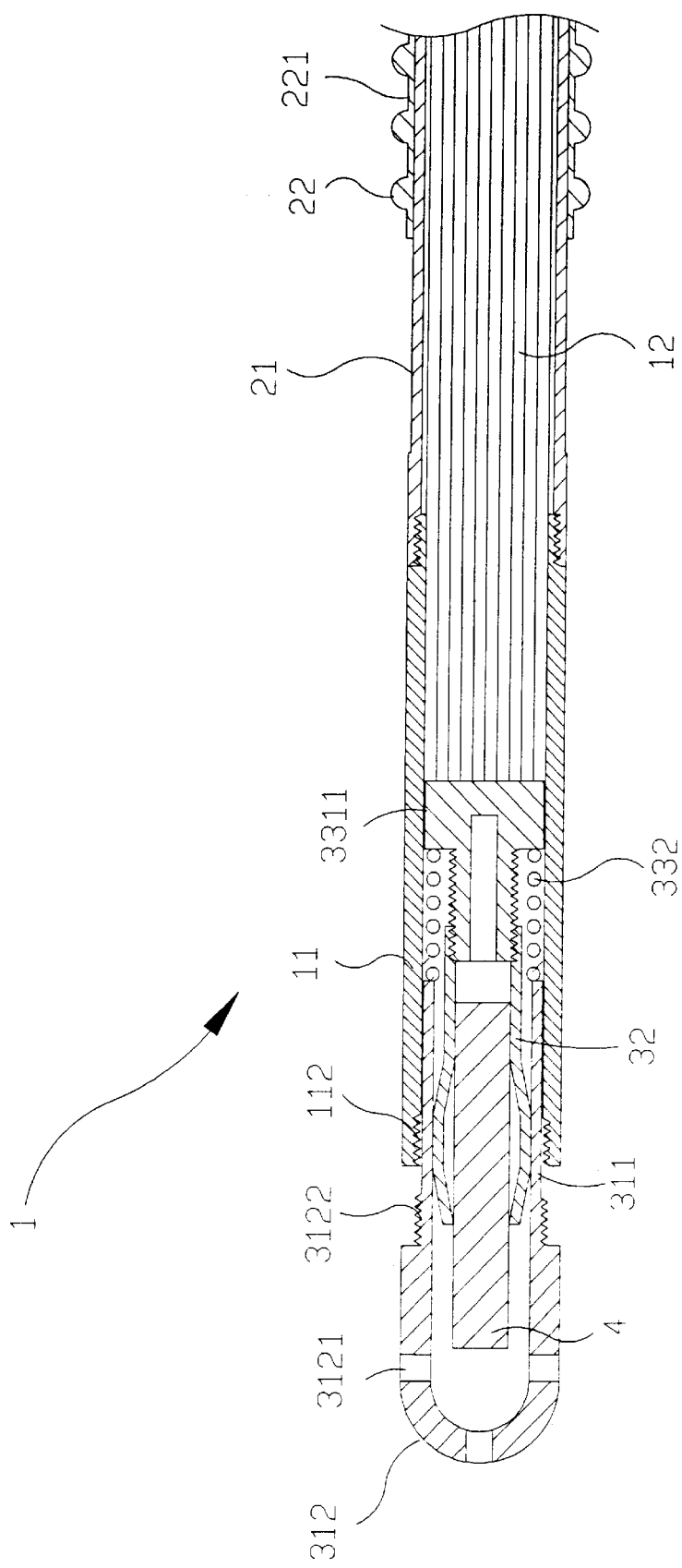
FIG. 13 is a cross section and in part cutaway view of FIG. 12.
Figure 14:
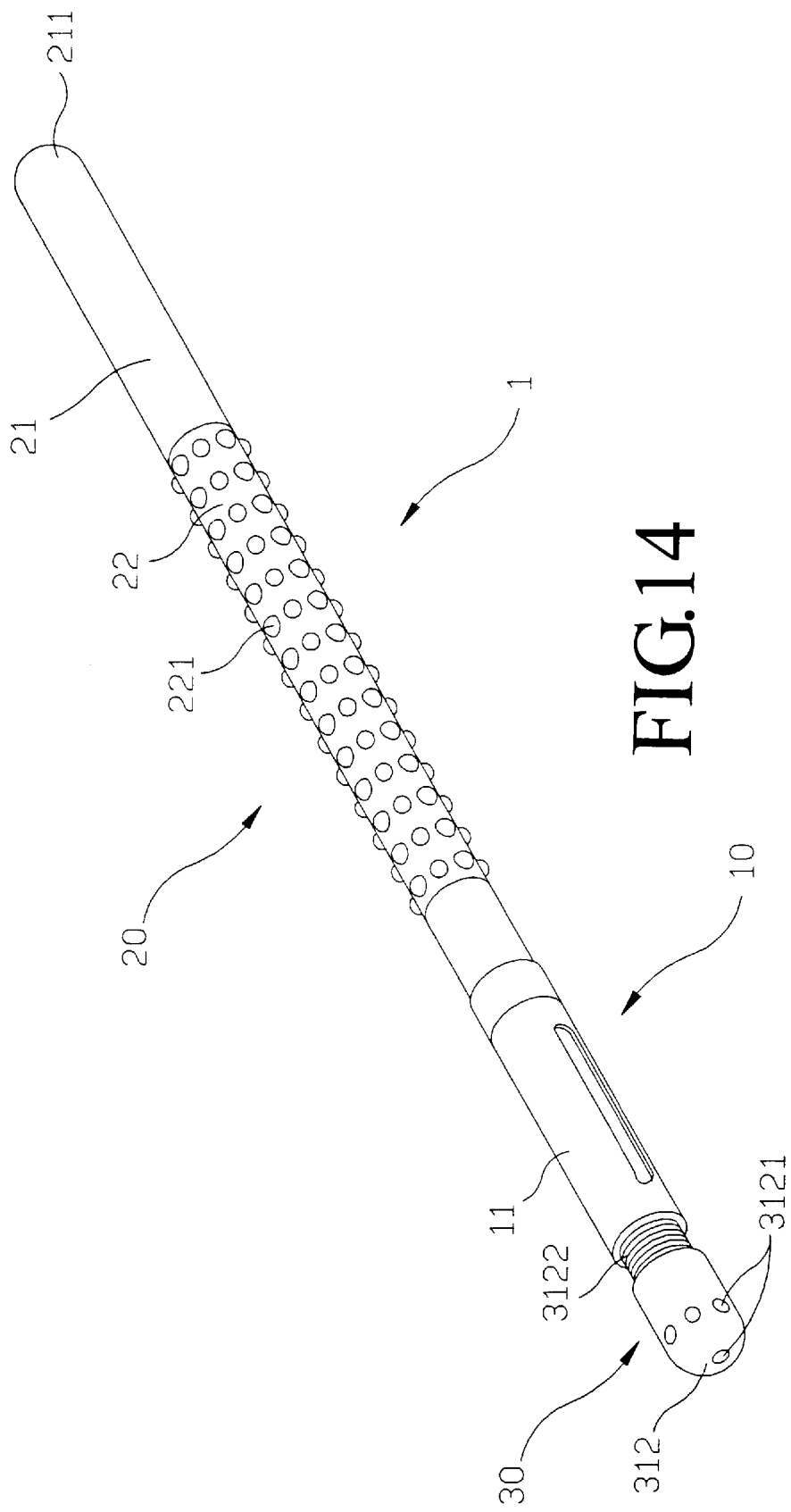
FIG. 14 is a perspective view of compression of the moxibustion instrument on the spring coil induced by an external force shown in FIG. 12.
Figure 15:
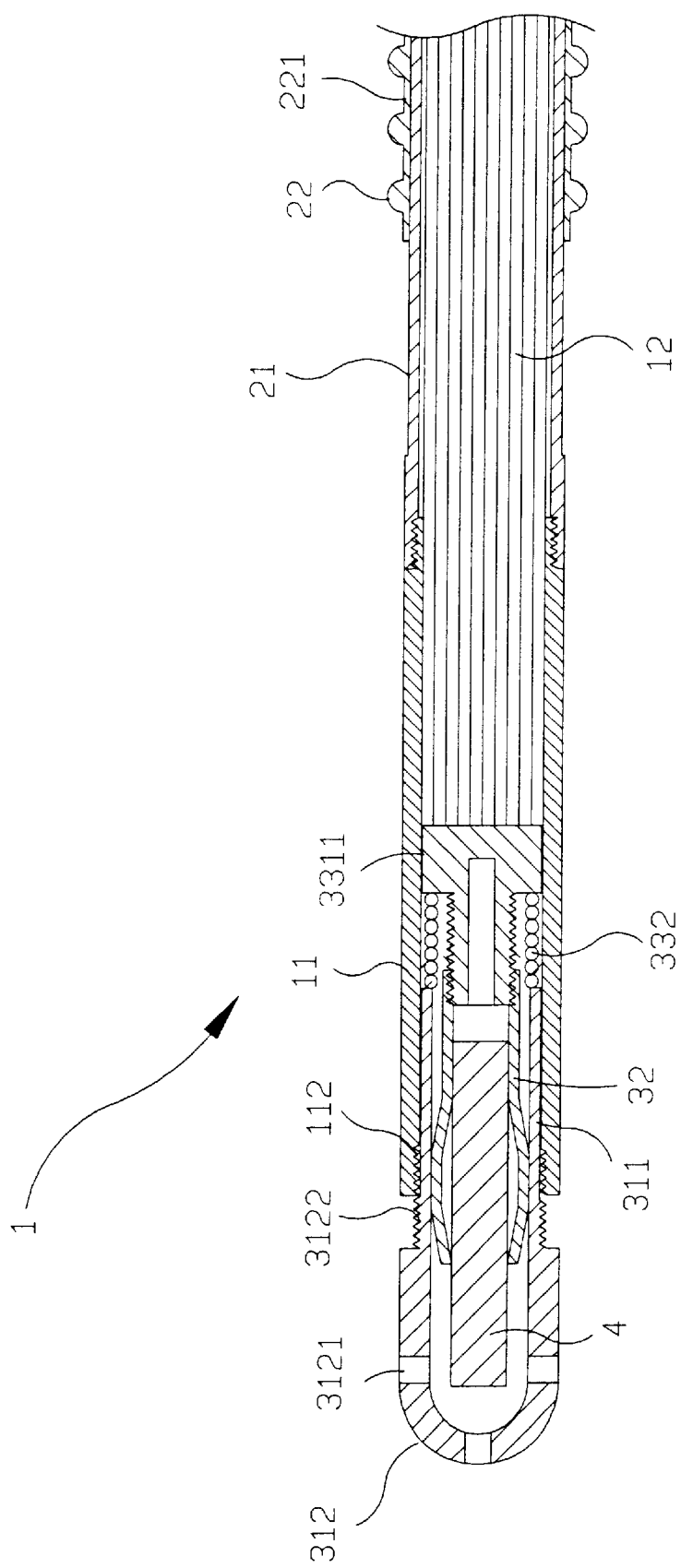
FIG. 15 is a cross section and in part cutaway view of FIG. 14.
Figure 18:
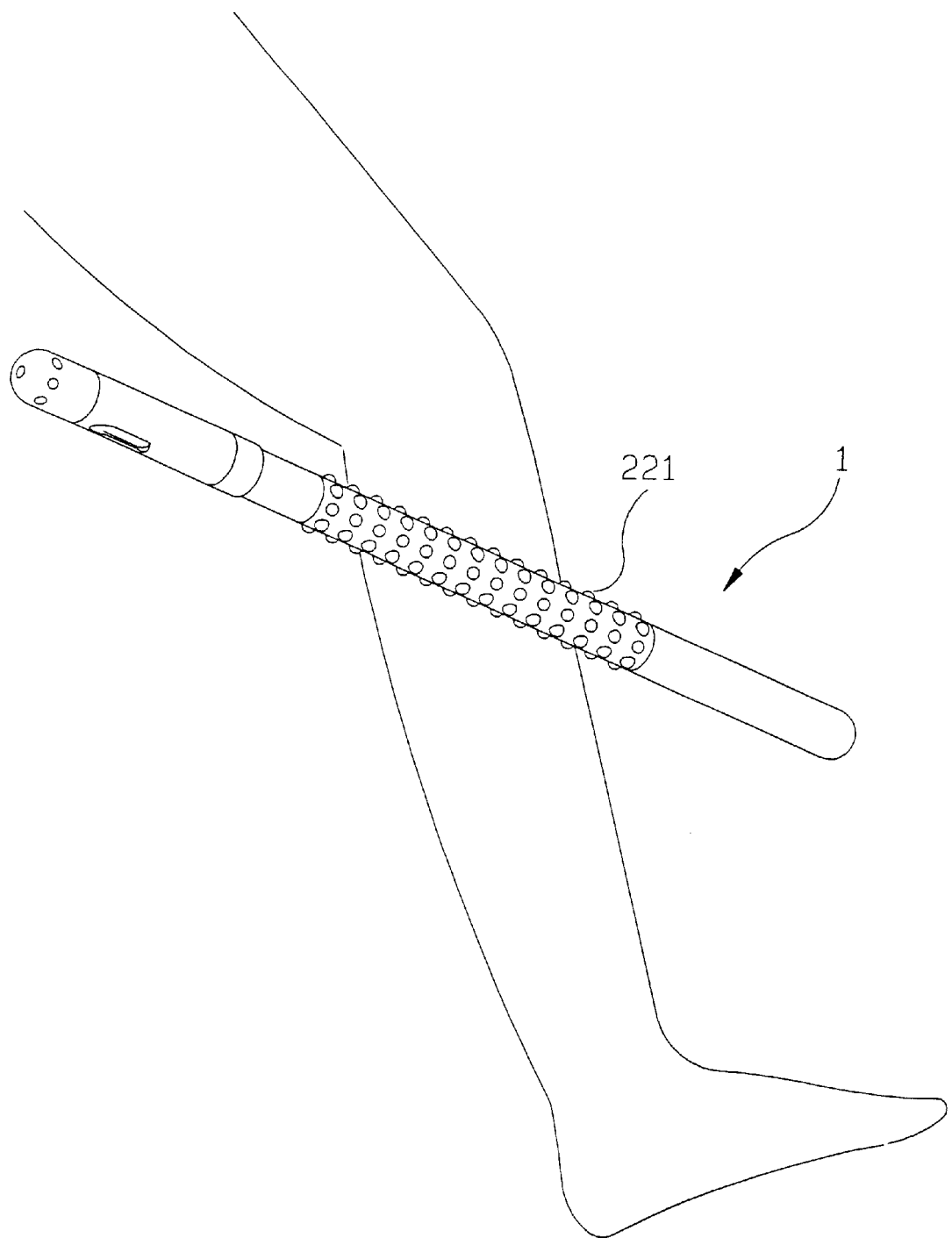
FIG. 18 is a plan view of many protuberances on the surface of sheath of fitness stick, as illustrated in FIGS. 2 and 5 can be used for massaging the external side of shanks.
Figure 19:
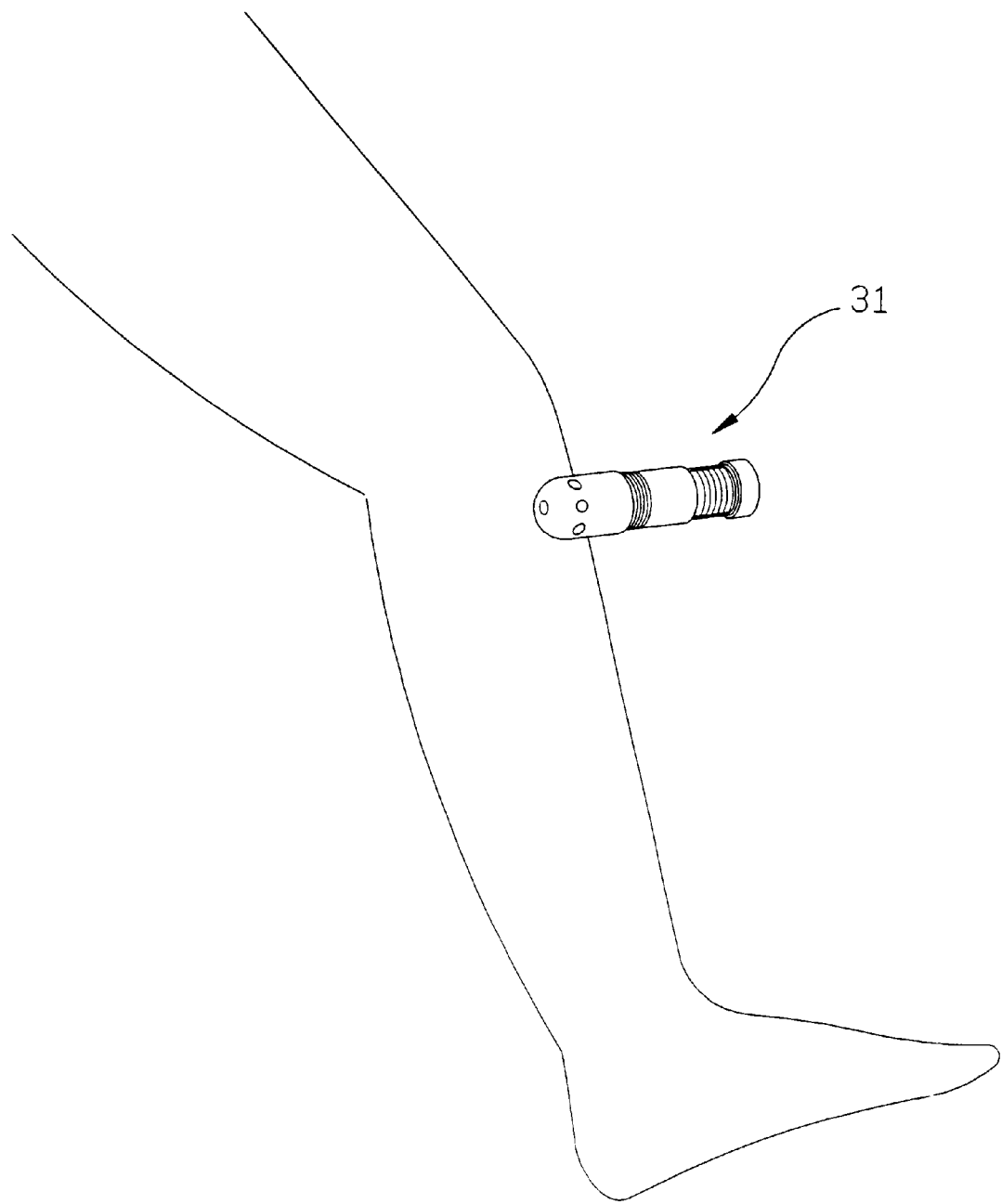
FIG. 19 is a plan view of the moxibustion instrument as illustrated in FIGS. 7 and 8, can be used for moxa treatment of Zusanli Acupoint on external side of shank.
Figure 20:
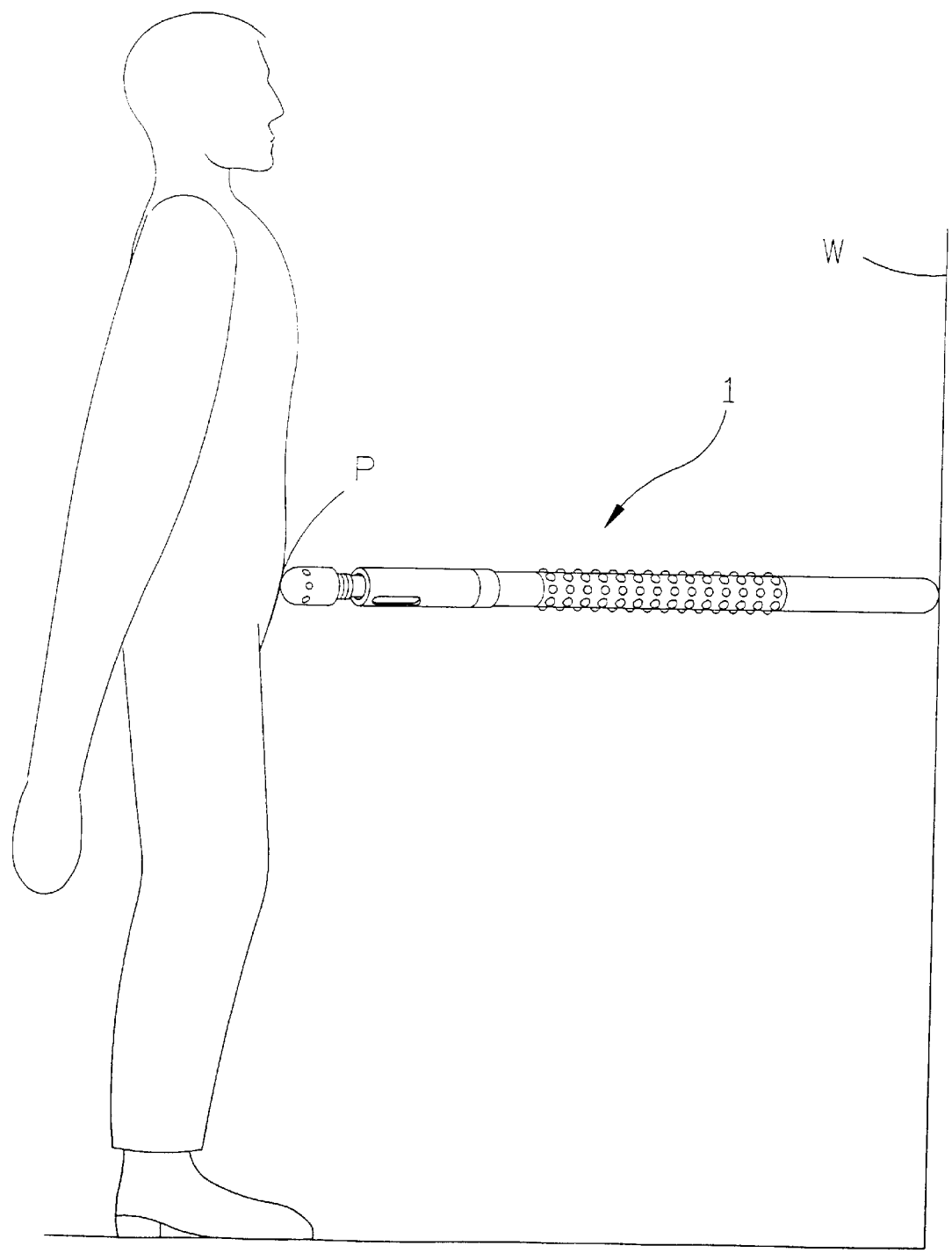
FIG. 20 is a plan view of one end of the fitness stick as illustrated in FIG. 12, gently contacts with Dantian Acupoint P and the other end contacts with the wall W.
Figure 21:
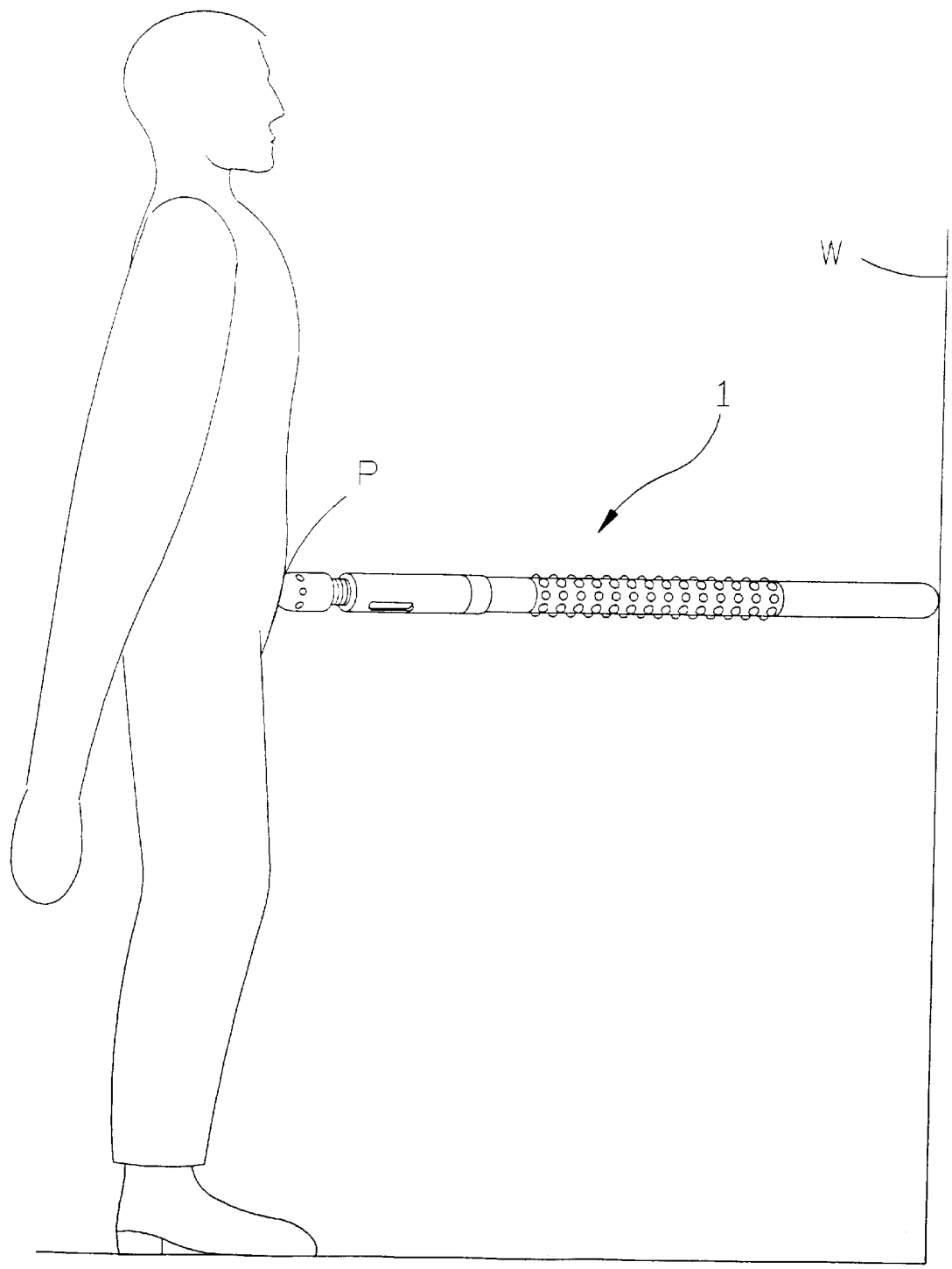
FIG. 21 is a plan view of one end of the fitness stick as illustrated in FIG. 14, firmly contacts with Dantian Acupoint P and the other end contacts with the wall W.
Figure 22:
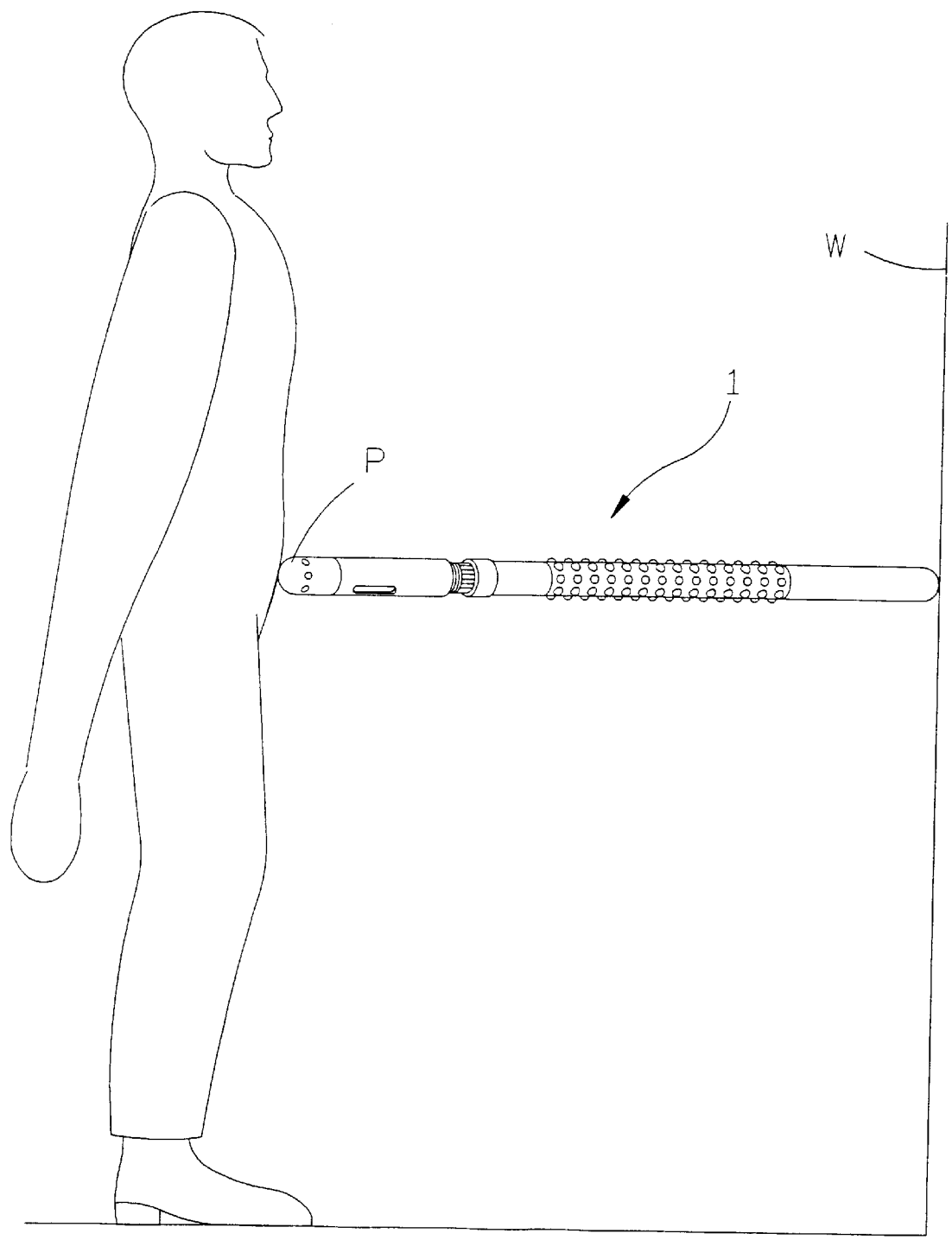
FIG. 22 is a plan view of one end of the fitness stick as illustrated in FIG. 16, can gently contacts with Dantian Acupoint P and the other end contacts with the wall W.
Figure 23:
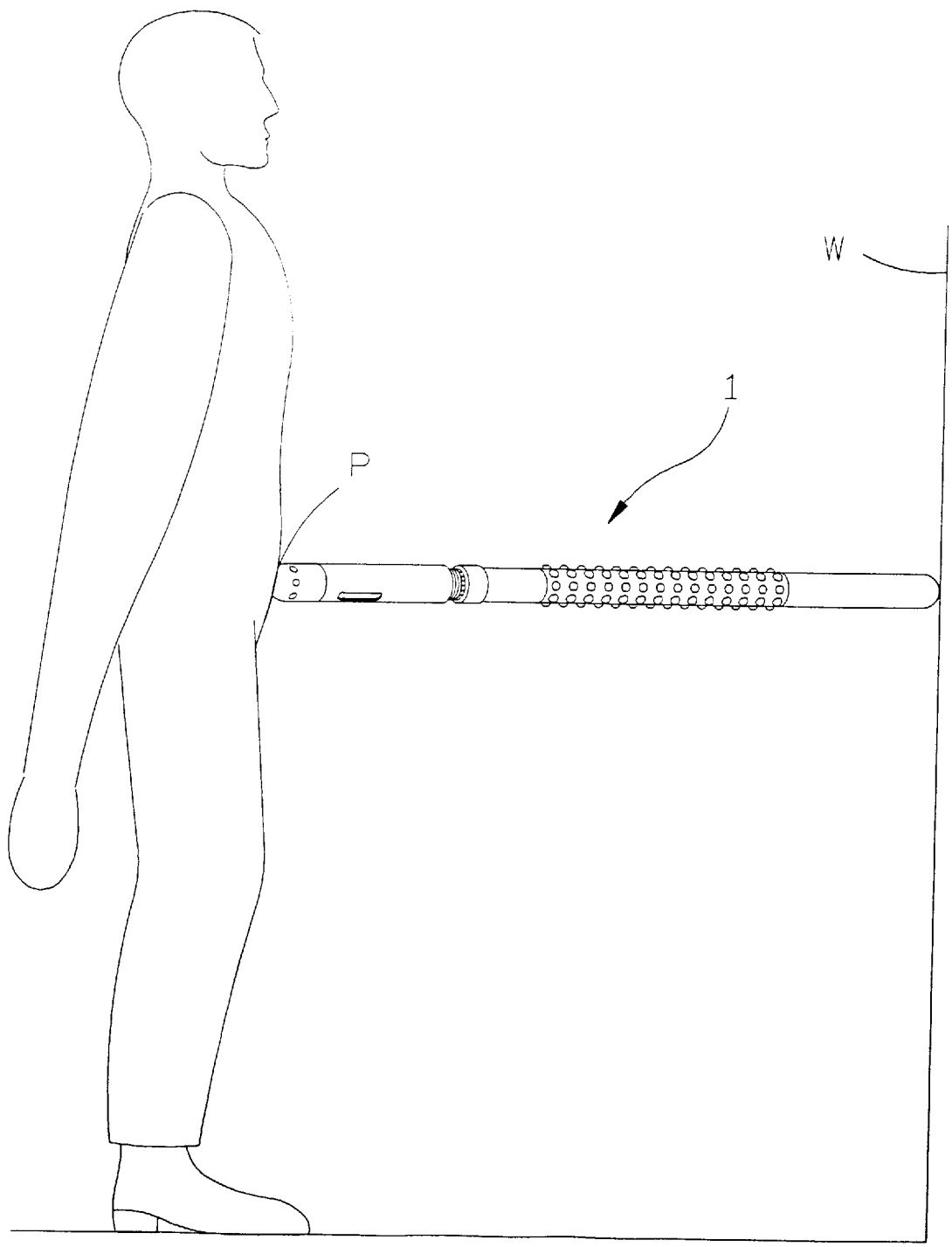
FIG. 23 is a plan view of one end of the fitness stick as illustrated in FIG. 17, firmly contacts with Dantian Acupoint P and the other end contacts with the wall W.

Furthermore, the unique features of configuration and structure of flapping bat 10, sheath 20 and moxibustion instrument 30 of fitness stick 1 can even bring the functions of massaging and moxibustion into effect. As shown in FIG. 18, many protuberances 221 on the surface of sheath 20 of fitness stick 1, as illustrated in FIGS. 2 and 5, can be used for massaging the external side of shanks. Or, as shown in FIG. 19, moxibustion instrument 30, as illustrated in FIGS. 7 and 8, can be used for moxa treatment of Zusanli Acupoint on external side of shank. As shown in FIG. 20, one end of fitness stick 1, as illustrated in FIG. 12, gently contacts with Dantian Acupoint P and the other end contacts with the wall W or, as shown In FIG. 21, one end of fitness stick 1, as illustrated in FIG. 14 firmly contacts with Dantian Acupoint P and the other end contacts with the wall W. Furthermore, as shown in FIG. 22, one end of fitness stick 1, as illustrated in FIG. 16, can gently contacts with Dantian Acupoint P and the other end contacts with the wall W. Or, as shown in FIG. 23, one end of fitness stick 1, as illustrated in FIG. 17, firmly contacts with Dantian Acupoint P and the other end contacts with the wall W. Performance of all abovementioned practice can urge the dilation of local vessels and increase blood and lymph circulation to ameliorate the nutrition status of local tissue and promote the metabolism and absorbance of retaining body fluid or pathological exudation. Furthermore, it can direct the blood flow in the deep tissue to the superficial layer. It can lead to retaining of some blood locally or hyperemia of deep tissue to alleviate hyperemia to urge the dispersion of pathological product. It can also affect the neurological function to excite or calm and inspire the spirit or relieve the tiredness. Furthermore, it can stretch the tendon and simulate the blood circulation and augment the vitality to bring out the effect of fitness and disease dispelling.

What is claimed is:

1. A fitness stick comprising a flapping bat, a sheath and a moxibustion instrument, said fitness stick having many protuberances on the surface of said sheath for massaging, the moxibustion instrument is assembled inside a handle of the flapping bat with a separable spring coil and could be separated from the stick for isolated use with both functions of moxibustion and massage.

2. A fitness stick as claimed in claim 1, wherein the flapping bat consists of said handle and a bundle of iron strip, the external edge of front end of handle is provided with a thread of screw, and the back end of handle is provided with a screw hole.

3. A fitness stick as claimed in claim 1, wherein the sheath consists of a covering shaft and a massaging sleeve, the front end of covering shaft is provided with a semicircle arc cap, and the back end of covering shaft is provided with a screw hole.

4. A fitness stick as claimed in claim 3, wherein the diameter of the covering shaft is the same as that of said handle of the flapping bat, and the length of the covering shaft is slightly longer than or the same as that of the bundle of iron strip located at the outside the handle of the flapping bat.

5. A fitness stick as claimed in claim 3, wherein the surface of massaging sleeve of said sheath is provided with many protuberances.

6. A fitness stick as claimed in claim 3, wherein the massaging sleeve is just able to cover the covering shaft to form said sheath with many surface protuberances for massaging function.

7. A fitness stick as claimed in claim 1, wherein the moxibustion instrument comprising a metal moxibustion cover, a clipping shaft and said spring coil, wherein the metal moxibustion cover consists of a hollow sleeve and a semicircle arc moxibustion cap.

8. A fitness stick as claimed in claim 7, wherein the back end and periphery of the semicircle arc moxibustion cap is provided with a plurality of vent holes, and the neck of semicircle arc moxibustion cap and the external edge of a back connection site of the hollow sleeve is provided with a thread of screw.

9. A fitness stick as claimed in claim 7, wherein the outer diameter of said hollow sleeve of metal moxibustion cover is equal to or slightly smaller than the inner diameter of said handle of said flapping bat.

10. A fitness stick as claimed in claim 7, wherein the front end of the clipping shaft of the moxibustion instrument is provided with a screw hole, and the back end of clipping shaft is provided with a spring clip.

11. A fitness stick as claimed in claim 7, wherein the spring coil of moxibustion consists of a screw and a spring, the spring is connected to the external edge of a screw shaft beneath a screw nut of said screw, and wherein the screw of spring coil is just right for screwing into the screw hole located at the front end of clipping shaft of moxibustion instrument to integrate all together, the spring of said spring coil being slipped on the external edge of clipping shaft, and a tip of said spring of said spring coil being slipped on the external edge of clipping shaft, is pushed against the front edge of said hollow sleeve of said metal moxibustion cover.

* * * * *